US007052907B2

(12) United States Patent
Shi et al.

(10) Patent No.: US 7,052,907 B2
(45) Date of Patent: May 30, 2006

(54) ADULT HUMAN DENTAL PULP STEM CELLS IN VITRO AND IN VIVO

(75) Inventors: Songtao Shi, Gaithersburg, MD (US); Stan Gronthos, Rockville, MD (US); Pamela Gehron Robey, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 238 days.

(21) Appl. No.: 10/333,522

(22) PCT Filed: Jul. 23, 2001

(86) PCT No.: PCT/US01/23053

§ 371 (c)(1),
(2), (4) Date: Sep. 22, 2003

(87) PCT Pub. No.: WO02/07679

PCT Pub. Date: Jan. 31, 2002

(65) Prior Publication Data

US 2004/0058442 A1   Mar. 25, 2004

Related U.S. Application Data

(60) Provisional application No. 60/219,989, filed on Jul. 21, 2000.

(51) Int. Cl.
*C12N 5/00* (2006.01)

(52) U.S. Cl. ....................................... 435/325; 435/378

(58) Field of Classification Search ................ 435/325, 435/378; 260/998.11; 433/215, 224
See application file for complete search history.

(56) References Cited

U.S. PATENT DOCUMENTS

| 5,885,829 | A  | * | 3/1999 | Mooney et al. | .............. | 435/325 |
| 6,767,740 | B1 | * | 7/2004 | Sramek et al. | .............. | 435/378 |
| 6,899,915 | B1 | * | 5/2005 | Yelick et al. | ............... | 427/2.26 |
| 2005/0019911 | A1 | * | 1/2005 | Gronthos et al. | ........... | 435/372 |
| 2005/0053585 | A1 | * | 3/2005 | Black et al. | ................ | 424/93.7 |
| 2005/0079470 | A1 | * | 4/2005 | Rutherford et al. | ......... | 433/226 |
| 2005/0106724 | A1 | * | 5/2005 | Schierholz et al. | ......... | 435/366 |

OTHER PUBLICATIONS

Bin P. Mineralization of Human Dental Pulp Cells in Continued Culture. Chinese J Stomatology 32(5)285-7, Sep. 1997.*
Boh. K. Role Synthetic Extracellular Matrix in Development of Engineered Dental Pulp. J Biomaterial Science Polymer Edition 9(7)749-764, 1998.*
Inoue T. Induction of Cartilage and Bone Formation by Cells from Explants of Various Oral Tissues in vitro. Bull Tokyo Dental College. 31(4)295-300, Nov. 1990.*
Azizi et al. Engraftment and migration of human bone marrow stromal cells implanted in the brains of albino rats—similarities to astrocyte grafts. *Proc Natl Acad Sci USA* 95:3908-3913 (1998).
Bennett et al. Adipocytic cells cultured from marrow have osteogenic potential. *Journal of Cell Science* 99:131-139 (1991).
Bianco et al. (1998) The bone marrow stroma in vivo: ontogeny, structure, cellular composition and changes in diseases., eds. Owen, M.A. & Beresford, J.N. (Cambridge University Press, Cambridge, UK), pp. 10-25.
Bianco et al. Uno, nessuno e centomila: searching for the identity of mesodermal progenitors. *Experimental Cell Research* 251:257-263 (1999).
Bianco et al. Marrow stromal stem cells. *Journal of Clinical Investigation* 105(12):1663-1668 (2000).
Buurma et al. Transplantation of human pulpal and gingival fibroblasts attached to synthetic scaffold. *Eur J Oral Sci* 107(4):282-289. (1999).
Casasco et al. Cell proliferation in developing human dental pulp: a combined flow cytometric and immunohistochemical study. *European Journal of Oral Sciences*, Denmark, Dec. 1997, vol. 105(6):609-613.
Cheng et al. Differentiation of human bone marrow osteogenic stromal cells *in vitro*: induction of the osteoblast phenotype by dexamethasone. *Endocrinology* 134: 277-286 (1994).
Couble et al. Odontoblast differentiation of human dental pulp cells in explant cultures. *Calcif Tissue Int* 66:129-138 (2000).
Doetsch et al. Subventricular zone astrocytes are neural stem cells in the adult mammalian brain. *Cell* 97:703-716 (1999).
Doherty et al. Vascular pericytes express osteogenic potential in vitro and in vivo. *Journal of Bone and Mineral Research* 13(5):828-838 (1998).
Feng et al. Genomic organization, chromosomal mapping, and promoter analysis of the mouse dentin sialophosphoprotein (Dspp) gene, which codes for both dentin sialoprotein and dentin phosphoprotein. (1998) *Journal of Biological Chemistry* 273(16):9457-9464 (1998).
Ferrari et al. Muscle regeneration by bone marrow-derived myogenic progenitors. *Science* 279:1528-1530 (1998).

(Continued)

*Primary Examiner*—Ralph Gitomer
(74) *Attorney, Agent, or Firm*—Needle & Rosenberg, P.C.

(57) ABSTRACT

The present invention provides a culture of isolated adult human dental pulp stem cells that can differentiate into dentin/pulp tissue that can be used to produce a tooth in a human being. The present invention further provides a method of regenerating human dentin/pulp tissue.

9 Claims, 12 Drawing Sheets

OTHER PUBLICATIONS

Friedenstein. Stromal mechanisms of bone marrow: cloning in vitro and retransplantation in vivo. *Immunology of Bone Marrow Transplantation* (Springer-Verlag, Berlin), pp. 19-29 (1980).

Friedenstein et al. Origin of bone marrow stromal mechanocytes in radiochimeras and heterotopic transplants. *Exp Hematol* 6:440-444 (1978).

Gorter de Vries et al. Characterization and immunocytochemical localization of dentine phosphoprotein in rat and bovine teeth. *Archives Oral Biology* 31(1):57-66 (1986).

Gronthos et al. The STRO-1 fraction of adult human bone marrow contains the osteogenic precursors. *Blood* 84(12):4164-4173 (1994).

Gronthos et al. Postnatal human dental pulp stem cells (DPSCs) in vitro and in vivo. *Proceedings of the National Academy of Sciences of the United States*, Dec. 2000, vol. 97 No. 25, pp. 13625-13630, no date given.

Holtgrave et al. Response of odontoblast-like cells to hydroxyapatite ceramic granules. *Biomaterials* 16:155-159 (1995).

Ishizeki et al. Calcification capacity of dental papilla mesenchymal cells transplanted in the isogenic mouse spleen. *Anat Rec* 226(3):279-287 (1990).

Johansson et al. Rapid communication neural stem cells in the adult human brain. *Experimental Cell Research* 253:733-736 (1999).

Kettunen et al. Responsiveness of developing dental tissues to fibroblast growth factors: expression of splicing alternatives of FGFR1, -2, -3, and of FGFR4; and stimulation of cell proliferation by FGF-2, -4, -8, and -9 *Developmental Genetics* 22:374-385 (1998).

Kitamura et al. Temporal and spatial expression of c-jun and jun-B proto-oncogenes in pulp cells involved with reparative dentinogenesis after cavity preparation of rat molars. *J Dent Res* 78:673-680 (1999).

Kuo et al. Collagen gene expression in human dental pulp cell cultures. *Archives of Oral Biology* 37(11):945-952 (1992).

Kuznetsov et al. Single-colony derived strains of human marrow stromal fibroblasts form bone after transplantation in vivo. (1997) *Journal of Bone and Mineral Research* 12:1335-1347 (1997).

Lennon et al. A chemically defined medium supports in vitro proliferation and maintains the osteochondral potential of rat marrow-derived mesenchymal stem cells. *Experimental Cell Research*; U.S., Jul. 1995, vol. 219 No. 1, pp. 211-222.

Lyaruu et al. Development of transplanted pulp tissue containing epithelial sheath into a tooth-like structure. *J Oral Pathol Med* 28(7):293-296 (1999).

MacDougall et al. Dentin phosphoprotein and dentin sialoprotein are cleavage products expressed froma single transcript coded by a gene on human chromosome 4 (1997) *Journal of Biological Chemistry* 272(2):835-842.

Magloire et al. An in vitro model of human dental pulp repair. *Journal of Dental Research*, U.S., Dec. 1996, vol. 75 No. 12, pp. 1971-1978.

Majors et al. Characterization of human bone marrow stromal cells with respect to osteoblastic differentiation . *J Orthop Res* 15(4):546-557 (1997).

Nakashima et al. Regulatory role of transforming growth factor-$\beta$, bone morphogenetic protein-2, and protein-4 on gene expression of extracellular matrix proteins and differentiation of dental pulp cells. *Developmental Biology* 162:18-28 (1994).

Onishi et al. Stimulation of proliferation and differentiation of dog dental pulp cells in serum-free culture medium by insulin-like growth factor. *Archives of Oral Biology* 44:361-371 (1999).

Owen. The marrow stromal cell system. *Marrow Stromal Cell Culture*. (Cambridge University Press, Cambridge), pp. 1-9 (1998).

Pittenger et al. Multilineage potential of adult human mesenchymal stem cells. *Science* 284:143-147 (1999).

Prime et al. Xenografts of human ameloblastoma tissue and odontogenic mesenchyme to hypothymic mice. *Transplantation* 33(5):561-562 (1982).

Ritchie et al. Cloning and sequence determination of rat dentin sialoprotein, a novel dentin protein. *Journal of Biological Chemistry* 269(5):3698-3702 (1994).

Robey. Stem cells near the century mark. *Journal of Clinical Investigation* 105(11):1489-1491 (2000).

Ruch. Odontoblast commitment and differentiation. *Biochem Cell Biol* 76:923-938 (1998).

Schultz et al. Skeletal muscle satellite cells. *Rev Physiol Biochem Pharmacol* 123:213-257 (1994).

Shiba et al. Effects of basic fibroblast growth factor on proliferation, the expression of osteonectin(SPARC) and alkaline phosphatase, and calcification in cultures human pulp cells. *Developmental Biology* 170:457-466 (1995).

Shiba et al. Differential effects of barious growth factors and cytokines on the syntheses of DNA, type I collagen, laminin, fibronectin, osteonectin/secreted protein, acidic and rich in cysteine (SPARC), and alkaline phosphatase by human pulp cells in culture. *Journal of Cell Physiology* 174:194-205 (1998).

Smith et al. Reactionary dentinogenesis. *Int J Dev Biol* 39:273-280 (1995).

Stanislawski et al. In vitro culture of human dental pulp cells: some aspects of cells emerging early from the explant. *Clinical Oral Investigations*, Germany, Sep. 1997, vol. 1 No. 3, pp. 131-140.

Tsukamoto et al. Mineralized nodule formation by cultures of human dental pulp-derived fibroblasts. *Archives of Oral Biology* 37(12):1045-1055 (1992).

Yokose et al. Establishment and characterization of a culture system for enzymatically released rat dental pulp cells. *Calcified Tissue International*, U.S., Feb. 2000, vol. 66 No. 2, pp. 139-144.

* cited by examiner

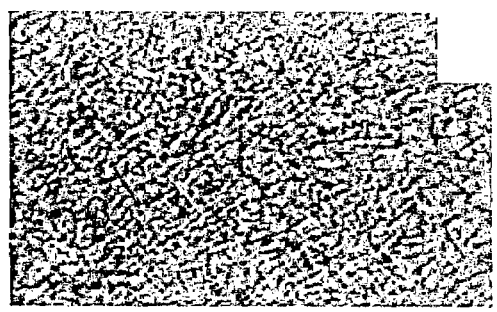
FIG.3A               FIG.3B
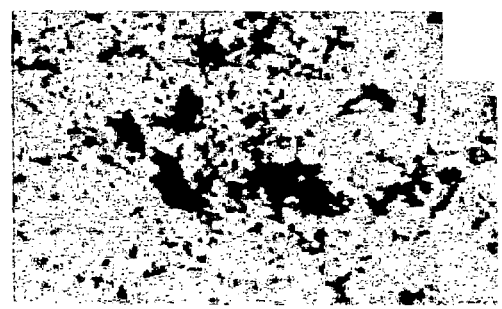
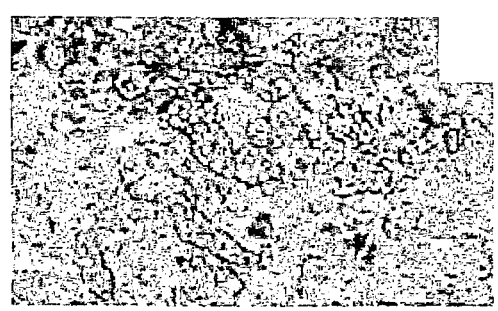
FIG.3C               FIG.3D

ADULT HUMAN DENTAL PULP STEM CELLS IN VITRO AND IN VIVO

CROSS REFERENCE TO RELATED APPLICATIONS

The present application is a 35 U.S.C. § 371 national phase application from, and claims priority to, international application PCT/US01/23053, filed Jul. 23, 2001 (published under PCT Article 21(2) in English), which claims priority to U.S. provisional application Ser. No. 60/219,989, filed Jul. 21, 2000, which applications are incorporated herein in full by this reference.

BACKGROUND OF THE INVENTION

1. Field of the Invention

The present invention relates to the field of restorative dentistry in humans. Specifically, the present invention relates to a population of cells that can differentiate into dentin/pulp and a method of regenerating dentin/pulp.

2. Background Art

During tooth formation, interactions between epithelial and dental papilla cells promote tooth morphogenesis by stimulating a subpopulation of mesenchymal cells to differentiate into odontoblasts, which in turn form primary dentin. Morphologically, odontoblasts are columnar, polarized cells with eccentric nuclei and long cellular processes aligned at the outer edges of dentin (1). Following tooth eruption, secondary dentin is formed by odontoblasts in response to general mechanical erosion or disruption, and through dentinal degradation caused by bacteria (2). These odontoblasts are thought to arise from the proliferation and differentiation of a precursor population, residing somewhere within the pulp tissue (3). Despite extensive knowledge of tooth development, and of the various specialized tooth-associated cell types, little is known about the characteristics and properties of their respective precursor cell populations in the post-natal organism.

Dentinal repair in the post-natal organism occurs through the activity of specialized cells, odontoblasts, that are thought to be maintained by an as yet undefined precursor population associated with pulp tissue (1). To date, the identification and isolation of an odontogenic progenitor population from adult dental pulp tissue has never been performed. It is known that in certain conditions, cultures of pulp cells derived from early developing dental root tissue and pulp tissue can develop an odontoblast-like appearance with the capacity to form mineralized nodules in vitro (4) a trait normally attributed to cultures of bone or bone marrow cells (5, 6). More is known about the characteristics of multipotent bone marrow stromal cells (BMSCs) and their potential to develop into osteoblasts, chondrocytes, adipocytes, myelosupportive fibrous-stroma, and perhaps even muscle and neural tissues (7–12). They are characterized by their high proliferative capacity ex vivo, while maintaining their ability to differentiate into multiple stromal cell lineages.

Because the prior art does not provide for regenerating dentin/pulp tissue or producing a human tooth for restorative purposes, there exists a great need to find a means for producing tissue that can differentiate into a functional tooth. In this study, a clonogenic, rapidly proliferative population of cells from adult human dental pulp was isolated. These dental pulp stem cells (DPSCs) were then compared to human bone marrow stromal cells (BMSCs), known precursors of osteoblasts. Although they share a similar immunophenotype in vitro, functional studies showed that DPSCs produced only sporadic, but densely calcified nodules, and did not form adipocytes, whereas BMSCs routinely calcified throughout the adherent cell layer with clusters of lipid-laden adipocytes. When DPSCs were transplanted into immunocompromised mice, they generated a dentin-like structure lined with human odontoblast-like cells that surrounded a pulp-like interstitial tissue. In contrast, BMSCs formed lamellar bone containing osteocytes and surface lining osteoblasts, surrounding a fibrous vascular tissue with active hematopoiesis and adipocytes. This study is the first to isolate post-natal human dental pulp stem cells that have the ability to form a dentin/pulp complex.

The present invention overcomes the previous limitations and shortcomings in the art by providing a human adult dental pulp stem cell (DPSC) that can differentiate into dentin/pulp tissue and a method for regenerating dentin/pulp and for producing a human tooth.

SUMMARY OF THE INVENTION

The present invention provides a culture of isolated adult human dental pulp stem cells.

The present invention also provides a method of regenerating human dentin/pulp tissue, comprising a) contacting a cell from a culture of isolated adult human dental pulp stem cells with hydroxyapatite/tricalcium phosphate and b) transplanting the cell from step a) into a mammal.

BRIEF DESCRIPTION OF THE DRAWINGS

FIGS. 3A–3D. Developmental potential in vitro. Adherent layers of cultured DPSCs (A & B), and BMSCs (C & D), are shown with Alizarin Red staining as a measure of calcium accumulation following 6 weeks of induction with L-ascorbate-2-phosphate and dexamethasone with inorganic phosphate (A & C). After 6 weeks in the same medium but without inorganic phosphate, lipid accumulation was noted in BMSCs (D), but not in DPSCs (B).

DETAILED DESCRIPTION OF THE INVENTION

Figure 1A:
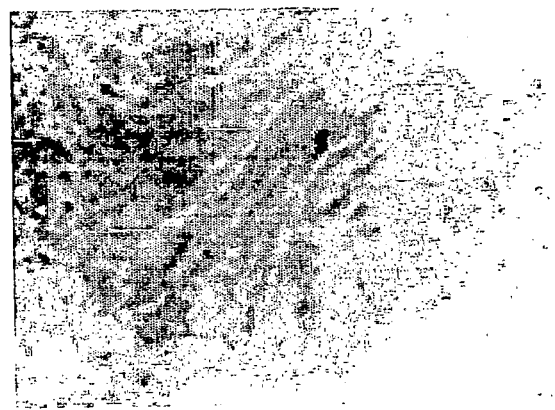
FIGS. 1A–1E. Colony forming efficiency and cell proliferation in vitro. Representative high (A) and low (B) density colonies after 14 days. The morphology is typical of fibroblast-like cells (C). The incidence of colony forming cells from dental-pulp tissue and bone marrow at various plating densities indicates that there are more clonogenic cells in dental pulp than in bone marrow (D). The number of BrdU positive cells was expressed as a percentage of the total number of cells counted for DPSCs and BMSCs (E). Statistical significance (*) was determined using the student t-test ($p \geq 0.05$).
Figure 1B:
Figure 1C:
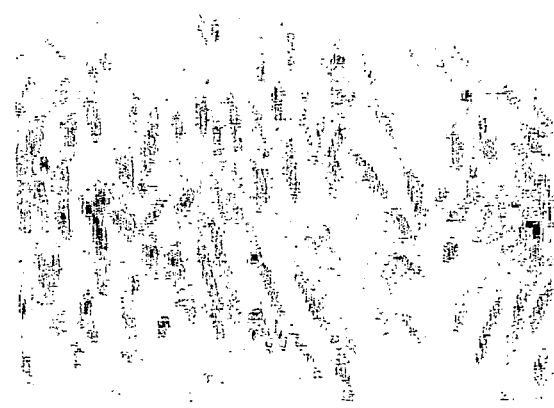

As used herein, "a," "an" or "the" may mean one or more. For example, "a" cell may mean one or more cells. Moreover, "the" cell may mean one or more than one cell.

The present invention provides a culture of isolated adult human dental pulp stem cells. Adult human dental pulp stem cells can be isolated from any human permanent tooth. Alternatively, the dental pulp stem cells of the invention can be isolated from a human subject at least about 18 years of age. "Isolated" as used herein means the cell of this invention is sufficiently free of contaminants or other cell types with which the cell of the present invention is naturally found. Moreover, the isolated cell of the present invention is present in such concentration as to be the only significant cell in the sample. "Isolated" does not require that the preparation be technically pure (homogeneous), but it is sufficiently pure to provide the cell in a form in which it can be used therapeutically or for research.

A "stem" cell is a cell that is multipotential, clonogenic, highly proliferative and capable of regenerating tissue. Thus, a stem cell has the ability to either influence other cells in its microenvironment to differentiate into a specific cell line or can itself differentiate into another cell type that has a specific function. Thus, an adult human dental pulp stem cell of the present invention is a cell obtained from the pulp tissue of a tooth from an adult human being. The stem cell of the present invention can differentiate into a more mature and functional cell, for example an odontoblast. An odontoblast is a cell found in the oral cavity of a mammal that produces dentin, a tissue that comprises and envelops a fibrovascular pulp and is covered by an outer enamel layer of a fully-formed tooth. The dental pulp stem cell of the present invention can produce a dentin/pulp tissue structure in vivo and in vitro. This structure is exemplified in FIG. 1.

The present invention provides a stem cell that is not adipogenic. Thus, the DPSC of the present invention does not differentiate into a fat cell. Moreover, the stem cell of the present invention does not produce bone sialoprotein. Thus, the stem cell of the present invention is not a bone marrow stem cell, a cell which can differentiate into a fat cell and produces bone sialoprotein. However, the stem cell of the present invention does produce odontoblast-specific dentin sialoprotein and dentin phosphoprotein, each protein encoded by the odontoblast-specific gene known as dentin sialophosphoprotein (DSPP).

The present invention provides a method of regenerating human dentin/pulp tissue, comprising a) contacting a cell from a culture of isolated adult human DPSCs with a mineral source and b) transplanting the cell from step a) into a mammal. The stem cell of the present method is mixed with a mineral source, for example, hydroxyapatite/tricalcium phosphate. This cell/mineral composition can then be transplanted into a mammal by methods known to a person of skill in the art. The stem cell/mineral composition can be transplanted into an immunocompromised mammal, for example a mouse, wherein the transplanted tissue can produce human dentin/pulp tissue that can be harvested for transplantation into a human being. The mammal may be a mouse, sheep, cow or any mammal used for transplantation studies and known to a person of skill in the art, including a human. Further, a human recipient of the stem cell/mineral composition can be an intermediate host from whom the dentin/pulp tissue can be harvested for further transplantation into another human dental patient. Alternatively, the human recipient of the stem cell/mineral composition can be both the donor and only recipient of the transplanted tissue.

Moreover, the present invention provides a method of producing human dentin/pulp tissue, comprising a) contacting a cell from a culture of isolated adult human DPSCs with a mineral source and b) transplanting the cell from step a) into a mammal. The stem cell of the present invention can be mixed with a mineral source, for example hydroxyapatite/tricalcium phosphate.

A person of skill in the art can transplant the stem cell/mineral composition into various sites of a mammal including subcutaneous tissue and oral tissue. It is contemplated that a person of skill in the art can transplant the stem cell/mineral composition into a tooth socket and, thereby, produce a dentin/pulp tissue in a human patient.

Moreover, the transplanted stem cell/mineral composition can be transplanted with or contacted in vitro with ameloblasts, cells that produce enamel, to produce a fully-formed functional tooth, comprising dentin/pulp tissue covered by enamel. Similarly, artificial crowns made from bio-compatible materials that mimic the hard enamel layer of teeth can be produced and used as a template. The transplanted stem cell/mineral composition can be transplanted directly into the cavity of an artificial crown where the cells can differentiate into dentin/pulp tissue in vivo, thereby forming a functional tooth.

The following examples are put forth so as to provide those of ordinary skill in the art with a complete disclosure and description of how the compositions and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. The present invention is more particularly described in the following examples which are intended as illustrative only since numerous modifications and variations therein will be apparent to those skilled in the art.

EXAMPLES

Subjects and Cell Culture.

Normal human impacted third molars were collected from adults (19–29 years of age) at the Dental Clinic of the National Institute of Dental & Craniofacial Research under approved guidelines set by the NIH Office of Human Subjects Research. Tooth surfaces were cleaned and cut around the cementum-enamel junction using sterilized dental fissure burs to reveal the pulp chamber. The pulp tissue was gently separated from the crown and root and then digested in a solution of 3 mg/ml collagenase type I (Worthington Biochem, Freehold, N.J.) and 4 mg/ml dispase (Boehringer Mannheim, GMBH, Germany) for one hour at 37° C. Single cell suspensions were obtained by passing the cells through a 70 µm strainer (Falcon, BD Labware, Franklin Lakes, N.J.). Bone marrow cells, processed from marrow aspirates of normal human adult volunteers (20–35 years of age), were purchased from Poietic Technologies, Gaithersburg, Md., and then washed in growth medium. Single cell suspensions (0.01 to $1\times10^5$/well) of dental pulp and bone marrow were seeded into 6-well plates (Costar, Cambridge, Mass.) with alpha Modification of Eagle's Medium (GIBCO BRL, Grand Island, N.Y.) supplemented with 20% fetal calf serum (Equitech-Bio Inc, Kerrville, Tex.), 100 µM L-ascorbic acid 2-phosphate (WAKO, Tokyo, Japan), 2 mM L-glutamine, 100 U/ml penicillin and 100 mg/ml streptomycin (Biofluids Inc, Rockville, Md.), then incubated at 37° C. in 5% $CO_2$. To assess colony-forming efficiency, day 14 cultures were fixed with 4% formalin, and then stained with 0.1% toluidine blue. Aggregates of ≧50 cells were scored as colonies. Conditions for the induction of calcified bone matrix deposition in vitro were as reported previously (6). The proliferation rate of sub-confluent cultures (first passage) of DPSCs and BMSCs was assessed by bromodeoxyuridine (BrdU) incorporation for 24 hours, using a Zymed Laboratories BrdU staining Kit (Vector Laboratories, Burlingame Calif.).

Immunohistochemistry.

Primary DPSCs and BMSCs were sub-cultured into 8-chamber slides ($2\times10^4$ cells/well) (NUNC Inc, Naperville, Ill.). The cells were fixed in 4% formalin, and then reacted with saturating levels of primary antibodies and the corresponding control antibodies using a Zymed broad spectrum immunoperoxidase kit (Vector Laboratories). Antibodies used were: Mouse (IgG) control (Caltag, Burlingame, Calif.). Rabbit (Ig) control, TUK4 (anti-CD14), QBEND 10 (anti-CD34), 2B11/PD7 (anti-CD45), M318 (anti-MyoD), 1A4 (anti-α smooth muscle actin), 2F11 (anti-neurofilament), (Dako, Carpinteria, Calif.); H9H11 (anti-CD44), 6G10 (anti-VCAM-1) (Dr. P. J. Simmons, HCCR, Adelaide, South Australia); CC9 (anti-MUC-18) (Dr. S. Gronthos NIDCR/NIH, MD); MAB1343 (anti-COL III), MAB1959 (anti-β1) (Chemicon, Temecula, Calif.); LF67 (anti-COL I), LF32 (anti-OC), BON-1 (anti-ON), LF100 (anti-BSP), LF123 (anti-OP) (Dr. L. Fisher, NIDCR/NIH, MD); MAB1104 (anti-COL II) (RDI, Flanders, N.J.); E-8 (anti-PPARγ), 147 (anti-FGF-2), (Santa Cruz, Santa Cruz, Calif.). Working dilutions of rabbit serum (1/500), monoclonal supernatants (1/4) and purified antibodies (10 µg/ml) were used.

Histochemistry.

Secondary DPSC and BMSC cultures were washed in PBS and then fixed with 4% formalin. Alkaline phosphatase activity was assessed using a Sigma in vitro alkaline phosphatase substrate kit (85L-2). Calcium deposits were detected by treatment with 2% Alizarin Red S (pH 4.2).

Transplantation.

Approximately $5.0\times10^6$ of DPSCs and BMSCs (third passage) were mixed with 40 mg of hydroxyapatite/tricalcium phosphate (HA/TCP) ceramic powder (Zimmer Inc, Warsaw, Ind.) and then transplanted subcutaneously into the dorsal surface of 10-week-old immunocompromised beige mice (NIH-bg-nu-xid, Harlan Sprague Dawley, Indianapolis, Ind.) as previously described (9). These procedures were performed in accordance to specifications of an approved small animal protocol (NIDCR #97-024). The transplants were recovered at 6 weeks post-transplantation, fixed with 4% formalin, decalcified with buffered 10% EDTA (pH 8.0), and then embedding in paraffin. Sections (5 m) were deparaffinized and stained with H&E.

RT-PCR.

Total RNA was prepared from collagenase/dispase digested cell suspensions of six week old DPSC transplants, using RNA STAT-60 (TEL-TEST Inc. Friendswood, Tex.). First-strand cDNA synthesis was performed using a first-strand cDNA synthesis kit (GIBCO BRL, Life Technologies) using an oligo-dT primer. First strand cDNA (2 µl) was diluted in a 50 µl PCR reaction of 1×PCR reaction buffer: 1.5 mM $MgCl_2$, 200 mM each dNTP, 0.2 units of AmpliTaq DNA Polymerase (Perkin-Elmer Inc, Norwalk, Conn.) and 10 pMol of each human specific primer sets: BSP (sense (SEQ ID NO.:1) 5'-CTATGGAGAGGACGCCACGC-CTGG-3' (S(antisense, (SEQ ID NO.:2) 5'-CATAGC-CATCGTAGCCTTGTCCT-3'), OC (sense, (SEQ ID NO.:3) 5'-CATGAGAGCCCTCACA-3'; antisense, (SEQ ID NO.:4) 5'-AGAGCGACACCCTAGAC-3'), DSPP (sense (SEQ ID NO.:5) 5'-GGCAGTGACTCAAAAGGAGC-3'; antisense, 5'-(SEQ ID NO.:6) TGCTGTCACTGTCACTGCTG-3'), GAPDH (sense, (SEQ ID NO.:7) 5'-AGCCGCATCT-TCTTTTGCGTC-3'; antisense (SEQ ID NO.:8) 5'-TCATATTTGGCAGGTTTTTCT-3'). The reactions were incubated in a PCR Express Hybaid thermal cycler (Hybaid, Franklin, Mass.) at 94° C. for 2 minutes for 1 cycle then 94° C./(45 sec), 56° C./(45 sec), 72° C./(60 sec) for 35 cycles, with a final 10 minute extension at 72° C. Following amplification, 10 µl of each reaction was analyzed by 1.5% agarose gel electrophoresis, and visualized by ethidium bromide staining.

In situ Hybridization.

A digoxigenin-labeled probe for human specific alu repetitive sequence was prepared by PCR using primers for alu as previously described (13). Similarly, a digoxigenin-labeled probe specific for human DSPP mRNA was also prepared using the DSPP primers under the same PCR conditions as described above. The specificity of both probes was verified by DNA sequencing. Unstained sections were deparaffinized and hybridized with either the digoxigenin-labeled alu probe (9) or the DSPP probe using the mRNAlocator-Hyb Kit (Cat # 1800; Ambion, Inc., Austin Tex.). After hybridization, the presence of both alu and DSPP mRNA in tissue sections was detected by immunoreactivity with an anti-digoxigenin alkaline phosphatase conjugated Fab fragments (Boehringer Mannheim).

Isolation of Clonogenic Populations of DPSCs.

Figure 1D:
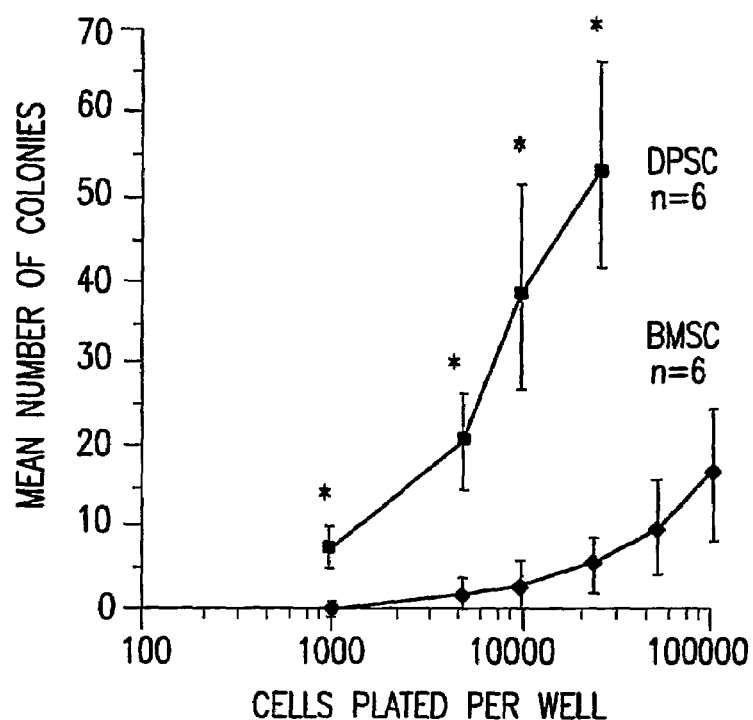
Figure 1E:
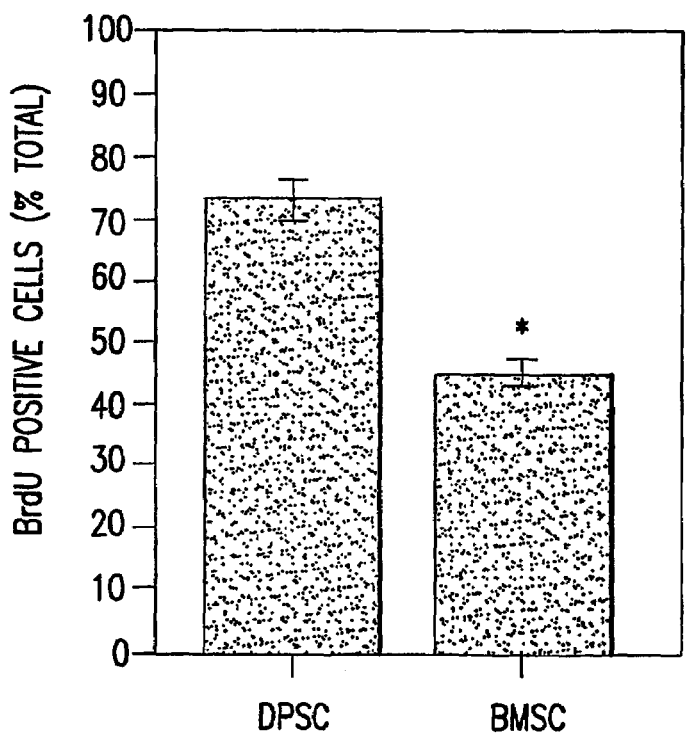
Figure 2A:
FIGS. 2A–2L. Immunophenotype of cultured DPSCs. Studies based on immunoperoxidase reactivity were performed on first passage cultures of DPSCs. Representative staining patterns are shown for: integrin $\beta 1$, (A); CD44, (B); collagen type I, (C); collagen type III, (D); FGF-2, (E); osteonectin, (F); osteocalcin, (G); MUC-18, (H); $\alpha$-smooth muscle actin, (I); osteopontin, (J); VCAM-1, (K). Endogenous, alkaline phosphatase activity is shown in (L).
Figure 2B:
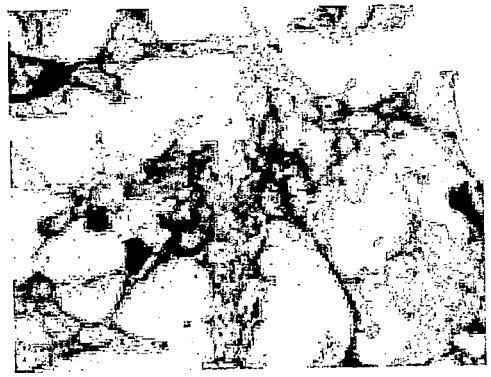
Figure 2C:
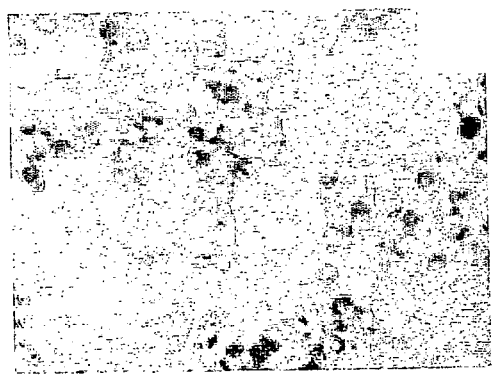
Figure 2D:
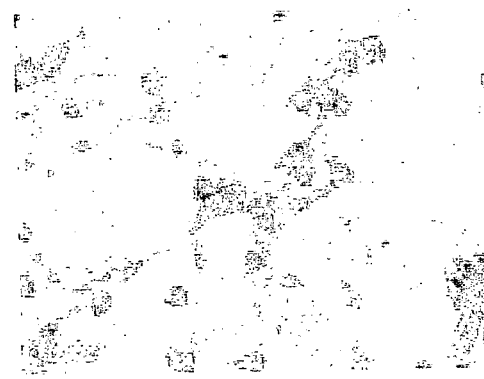
Figure 2E:
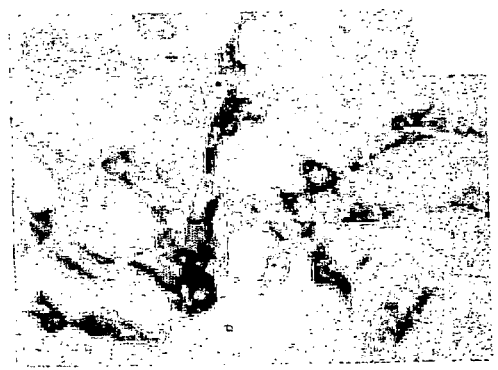
Figure 2F:
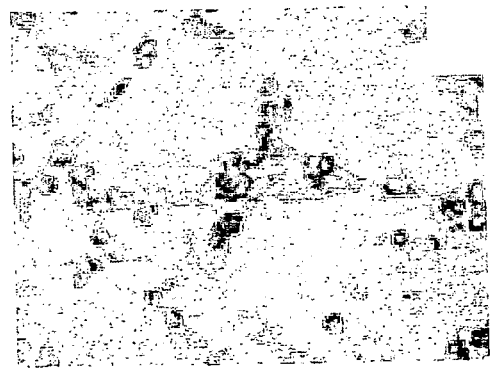
Figure 2G:
Figure 2H:
Figure 2I:
Figure 2J:
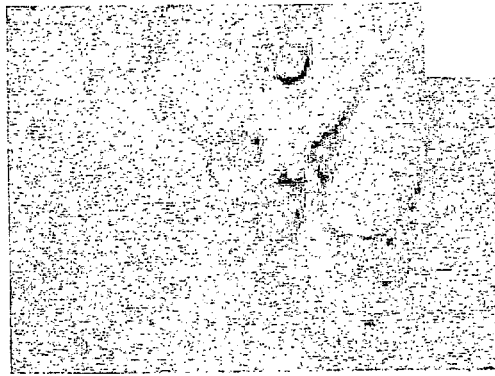
Figure 2K:
Figure 2L:
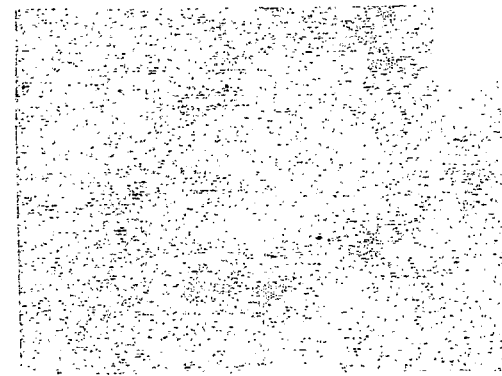

Osteoprogenitors can be isolated from aspirates of bone marrow by their ability to adhere to a plastic substratum, and with appropriate stimulation, begin to proliferate (13–15). Each colony originates from a single progenitor cell (colony forming unit-fibroblast, CFU-F) and displays a wide variation in cell morphology and growth potential (13–18). Herein, the presence of a clonogenic cell population in dental pulp tissue (FIGS. 1A and B) is demonstrated for the first time. The cells within each colony were characterized by a typical fibroblast-like morphology (FIG. 1C) analogous to the progeny of human bone marrow CFU-F (19). The frequency of colony forming cells derived from dental pulp tissue (range 22 to 70 colonies per $10^4$ cells plated) was significantly higher in comparison to the incidence of bone marrow CFU-F (range 2.4 to 3.1 colonies/$10^4$ cells plated) over similar plating densities (0.1 to 2.5×$10^4$ cells plated) (FIG. 1D). In addition, the number of proliferating cells in DPSC cultures was also significantly higher (mean 72% BrdU positive cells±3.48 SEM, n=3) when compared to BMSC cultures (46% BrdU positive cells±1.96 SEM, n=3) using the BrdU uptake method (t-test $p \leq 0.05$) (FIG. 1E).

Characterization of the Immunophenotype of DPSCs in vitro.

Immunohistochemical studies were performed to characterize the progeny of the DPSC and BMSC clonogenic populations, using a large panel of antibodies specific to known antigens associated with different phenotypes. Typical immunoreactivity profiles for both cell populations are shown in Table 1. Primary cultures of DPSC and BMSC failed to react with the hematopoietic markers CD14 (monocyte/macrophage), CD45 (common leukocyte antigen), CD34 (hematopoietic stem/progenitor cells/endothelium) and other markers such as MyoD (smooth muscle), neurofilament (nerve), collagen type II (cartilage) and PPARγ (fat). In general, DPSCs and BMSCs exhibited a similar expression pattern for a variety of markers associated with endothelium (VCAM-1 and MUC-18), smooth muscle (α-smooth muscle actin), bone (alkaline phosphatase, type I collagen, osteonectin, osteopontin, osteocalcin) and fibroblasts (type III collagen, FGF-2). The bone matrix protein, bone sialoprotein, was absent in DPSC cultures, but present at low levels in BMSC cultures. Representative immunoreactivity patterns for DPSC are shown in (FIG. 2). Many of the markers were not uniformly expressed, but found in subsets of cells, indicating that the DSPC population is heterogeneous, as has been shown for the BMSC population.

Differentiation Potential of DPSCs in vitro.

Long-term cultures (5 to 6 weeks) of DPSCs grown in the presence of L-ascorbate-2-phosphate, the glucocorticoid, dexamethasone, and inorganic phosphate demonstrated the capacity to form Alizirin Red positive condensed, nodules with high levels of calcium (FIG. 3A). The deposits were sparsely scattered throughout the adherent layer as single mineralized zones. In contrast, BMSC cultures produced extensive sheets of calcified deposits over the entire adherent layer following 3 to 4 weeks of induction (FIG. 3C). After 6 weeks of stimulation with dexamethasone, there was no evidence of adipogenesis in primary DPSC cultures (FIG. 3C) where as clusters of lipid-containing adipocytes were detected in primary cultures of BMSC as early as two weeks (FIG. 3D).

Figure 4A:
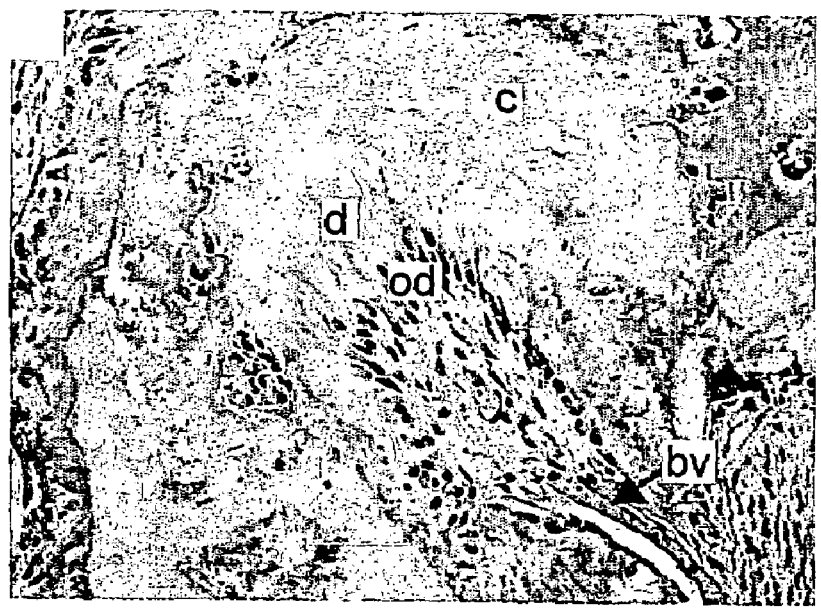
FIGS. 4A–4F. Developmental potential in vivo. Cross sections are representative of DPSC transplants, (A, C, D) and BMSC transplants, (B, E, F) 6 weeks post-transplantation and stained with hematoxylin and eosin. In the DPSC transplants, the HA/TCP carrier surfaces (c) are lined with a dentin-like matrix (d), surrounding a pulp-like tissue with blood vessels (bv) and an interface layer of odontoblast-like cells (od) (A). A magnified view of the dentin matrix (d) highlights the odontoblast-like layer (od) and odontoblast processes (arrow) (C). Polarized light demonstrates perpendicular alignment (dashed lines) of the collagen fibers to the forming surface (D). In BMSC transplants, lamellar bone (b) is formed on the HA/TCP surfaces (c) and surrounds a vascular, hematopoietic marrow organ (hp) with accumulated adipocytes (a) (B). A magnified view shows that the new bone contains osteocytes (oc), embedded within the calcified matrix, and osteoblasts (ob) lining the bone surfaces (E). With polarized light, collagen fibrils are seen to be deposited parallel with the forming surface (dashed lines) (F).
Figure 4B:
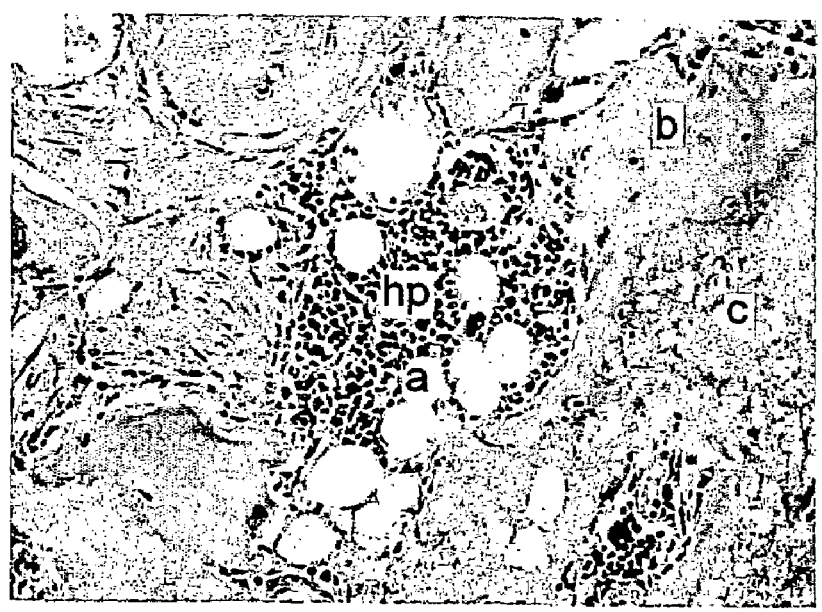
Figure 4C:
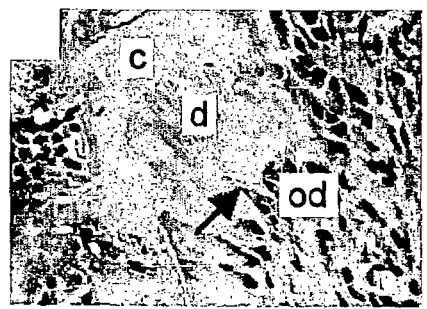
Figure 4D:
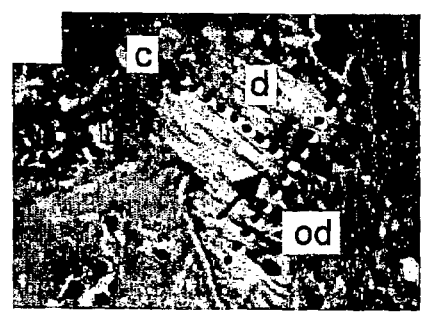
Figure 4E:
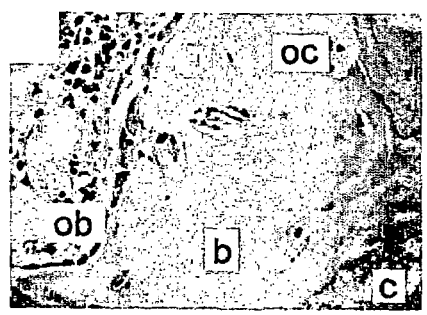
Figure 4F:
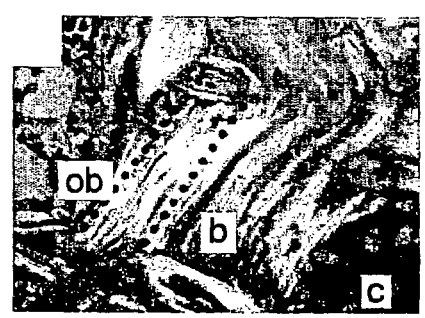
Figure 5A:
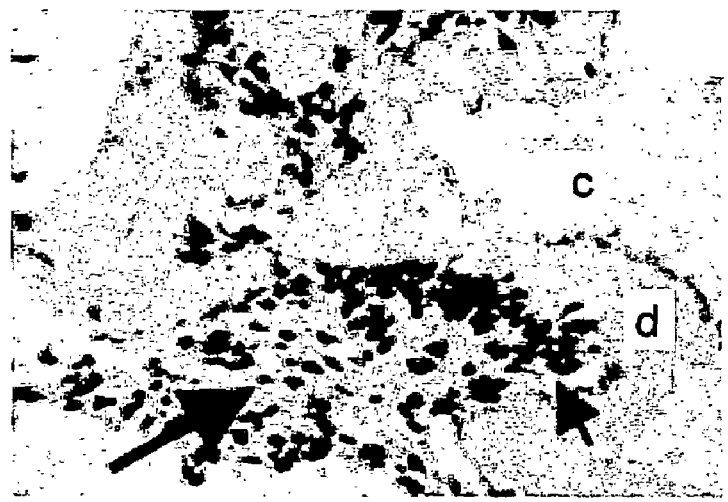
FIGS. 5A–5B. In situ hybridization for the human specific alu DNA sequence. Alu positive cells in the pulp tissue (large arrow) and odontoblast-like layer (small arrow) adjacent to the dentin matrix (d) are easily recognized in 6 week DPSC transplants (A). Osteocytes encased in the new bone matrix (small arrow) and the osteoblasts lining the bone (b) surfaces (large arrow) show positive reactivity with the alu probe in the BMSC transplants (B). Hematopoietic elements (hp) in the marrow-like organ fail to show reactivity with the alu probe.
Figure 5B:
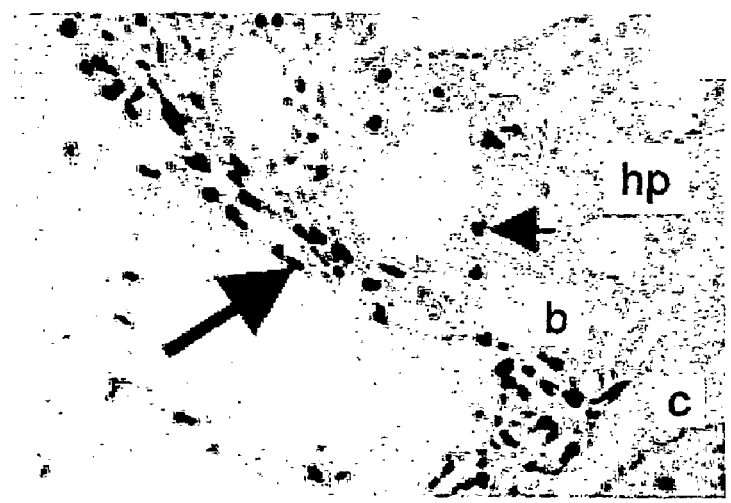
Figure 6A:
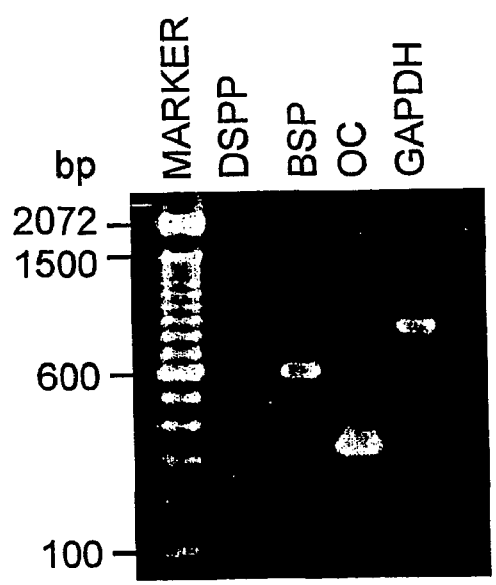
FIGS. 6A–6C. Expression of the human specific Dentin Sialophosphoprotein (DSPP), osteocalcin (OC), bone sialoprotein (BSP) mRNA in DPSC transplants. Transcripts for DSPP, BSP, OC and GAPDH were detected by RT-PCR using total RNA isolated from 6 week old DSPC transplants (A). DSPP positive cells were also found in the pulp tissue and odontoblast layer (arrow) adjacent to the dentin matrix (d) by in situ hybridization (B). Specificity of the probe was verified by hybridization in the odontoblast layer (arrow) of human dental pulp (p) tissue (C). No reactivity of the DSPP specific probe was detected in human bone, bone marrow and muscle tissue.
Figure 6B:
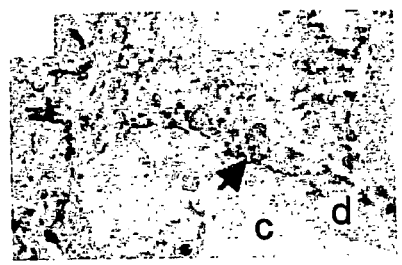
Figure 6C:
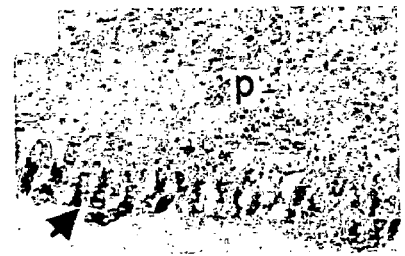
Figure 7A:
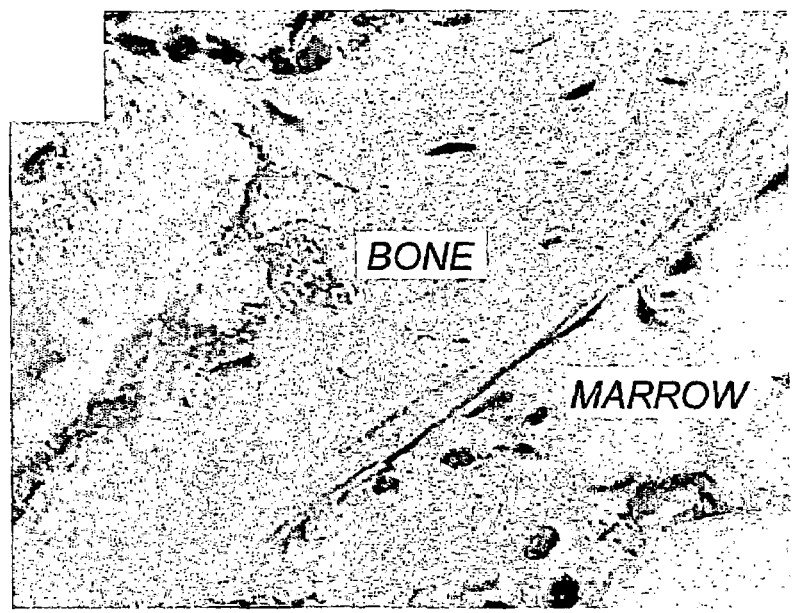
FIGS. 7A–7D. Immunohistochemical staining of human DSPP. Bone and associated marrow elements were negative for DSPP antibody staining in BMSC transplants (A). Newly formed dentin was positive for DSPP antibody staining in DPSC transplants (arrow, B). Normal human dentin and odontoblasts in human pulp were positive for DSPP (C and D, respectively).
Figure 7B:
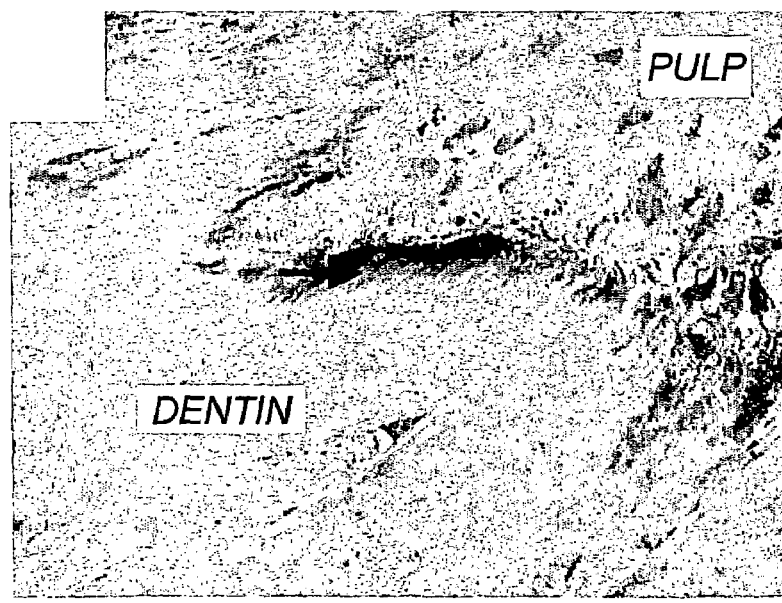
Figure 7C:
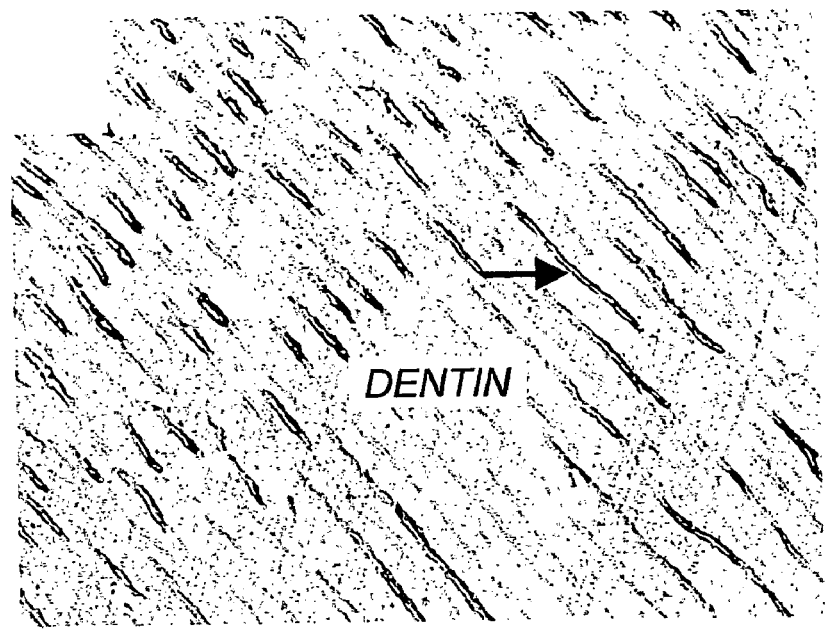
Figure 7D:
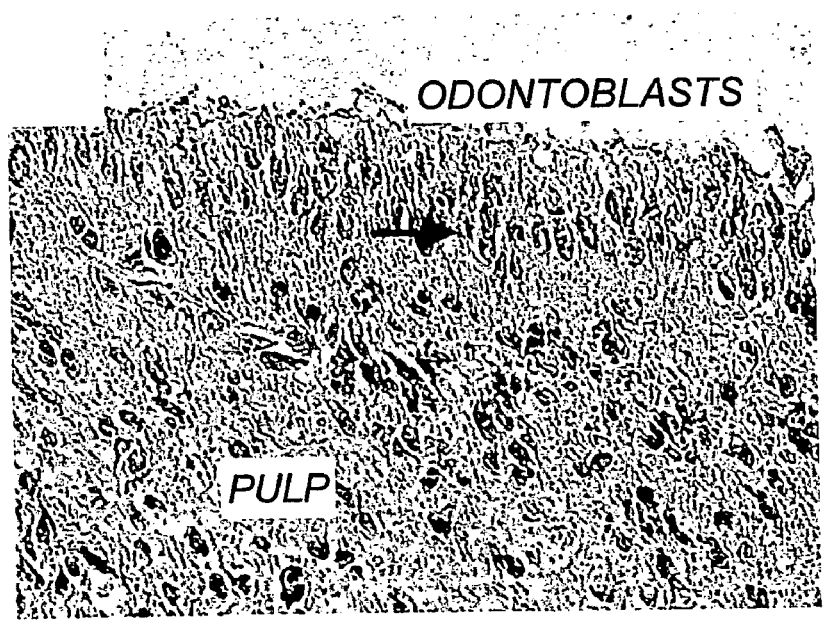

Ex vivo expanded DPSCs can generate a dentin/pulp structure in vivo. Because complete developmental potential and formation of an appropriate histological structure often can not be fully realized in vitro, DPSCs were transplanted in conjunction with hydroxyapatite/tricalcium phosphate (HA/TCP) powder into immunocompromised nice. After 6 weeks post-transplantation, DPSCs generated a dentin-like structure lining the surfaces of the HA/TCP particles, comprised of a highly ordered collagenous matrix deposited perpendicular to the odontoblast-like layer when viewed by polarized light (FIGS. 4A, C, D). Immunological studies demonstrated that the matrix was predominantly composed of collagen type I. The odontoblast-like cells extended cytoplasmic processes into the dentinal matrix, which interfaced with a pulp-like interstitial tissue infiltrated with blood vessels. The pulp and odontoblast-like cells were found to be of donor origin based on their reactivity to the human alu specific probe (FIG. 5A). Furthermore, the DPSC transplants expressed human specific transcripts for dentin matrix components, including bone sialoprotein, osteocalcin and dentin sialophosphoprotein (DSPP) by RT-PCR and in situ hybridization (FIG. 6). The corresponding BMSC transplants formed distinct lamellae of bone on the surface of the HA/TCP where the collagen fibers were aligned parallel to the osteoblasts on the bone forming surfaces (FIGS. 4B, E, F). Osteocytes, entombed within the bone matrix, and osteoblasts were also found to be of donor origin (FIG. 5B). Newly formed bone surrounded an interstitial tissue that was infiltrated by a sinusoid network resembling a marrow-like organ, with extensive areas of active hematopoiesis and adipocyte accumulation. Interestingly, the DPSC transplants failed to support any hematopoiesis or to initiate adipocyte formation even 4 months post transplantation.

Immunohistochemical Staining for Human DSPP.

Transplantation of DPSCs and BMSCs was performed as described above. The transplants were recovered 8 weeks post-transplantation and fixed for 24 hours with 4% freshly prepared paraformadehyde, and decalcified for 7 days with 10% EDTA (pH 8.0). The transplants were then transferred to 70% ethanol and embedded into paraffin block. The DSPP antibody was from Dr. Larry Fisher (NIDCR/NIH). After deparaffinization, rehydration, and elimination of endogenous peroxidase, the sections were incubated with the DSPP primary antibody at room temperature for 1 hour. Then Histostain SP Kits were used for second antibodies and enzyme conjugate incubation according to the instruction (Zymed Laboratories Inc. South San Francisco, Calif., USA). Human pulp and demineralized dentin tissues were used as positive controls. This procedure showed that newly formed dentin in DPSCs transplants is positive for dentin specific DSPP antibody (FIG. 7). This is additional evidence that human DPSCs differentiate into odontoblasts to regenerate human dentin in vivo.

Trichrome Staining of Dentin Formation in DPSC Transplants.

Figure 8A:
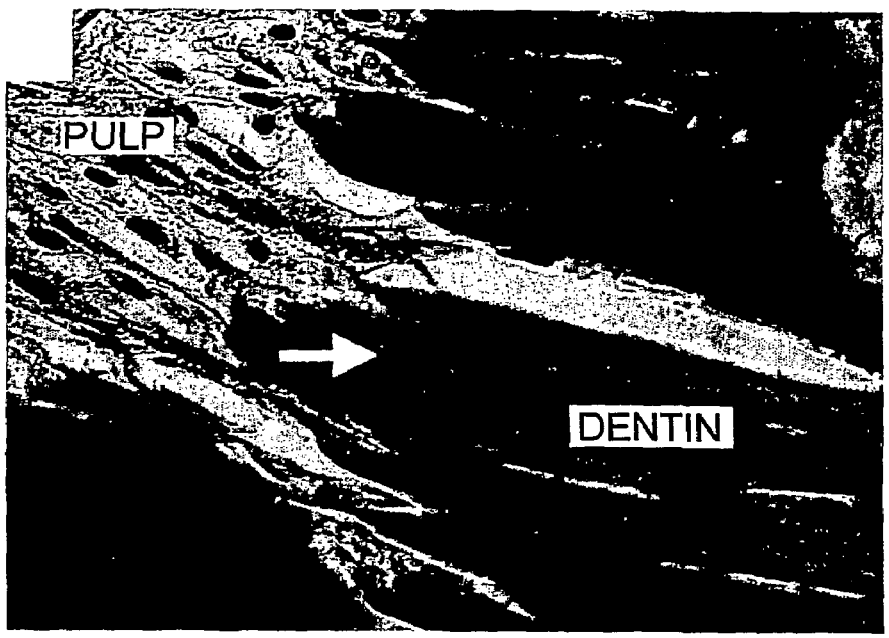
FIGS. 8A–8B. Dentin formation in DPSC transplants. Trichrome (blue) staining of dentin (arrow) in eight week old human DPSC transplants (A). Transverse section of a normal tooth depicting trichrome staining (arrow) of dentin in situ (B).
Figure 8B:
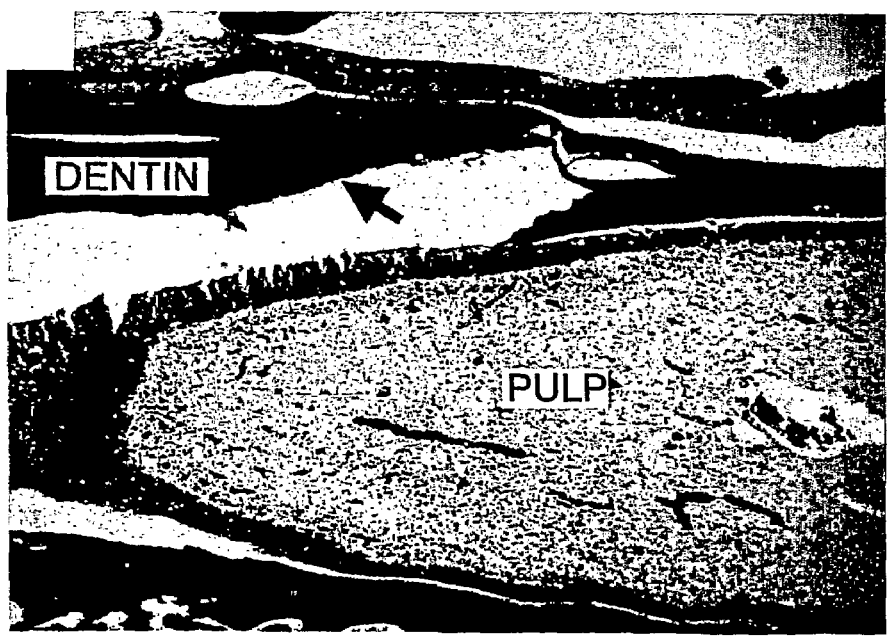

Transplantation of DPSCs and BMSCs was performed as described above. Eight week old human DPSC transplants were fixed for 24 hours with 4% freshly prepared paraformaldehyde, and transferred into 70% ethanol and plastic embedded. The Trichrome staining (GOMORI) kit (Sigma, #HT10516) was used for the staining according to the manufacturer's protocol. Normal tooth plastic-embedded sections were used as positive controls. This staining showed that DPSCs regenerate dentin comprising similar mineralized collagen structure as normal human dentin (FIG. 8).

The data presented here demonstrate for the first time that post-natal dental pulp contains cells that are clonogenic, highly proliferative and capable of regenerating a tissue, properties that effectively define them as stem cells. Although muscle, nervous tissue, and dentin-associated tissue do not remodel during post-natal life, they all contain stem cells that have the ability to differentiate in response to injury. The transplantation of human DPSCs into immunocompromised mice provides a new model by which to further characterize these stem cells. Furthermore, the amount of dentin and pulp-like tissue formed in these transplants far exceeds the amount that would be generated in situ during the lifetime of an organism. Consequently, the present isolation of a large number of DPSCs from a single tooth allows for dentinal repair of a number of teeth. Further, through the use of carriers with appropriate shape and composition in conjunction with ex vivo expanded DPSCs, the fabrication of a viable dental implant is provided.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Smith, A. J., Cassidy, N., Perry, H., Begue-Kirn, C., Ruch, J. V. & Lesot, H. (1995) *Int J Dev Biol* 39, 273–80.
2. Kitamura, C., Kimura, K., Nakayama, T. & Terashita, M. (1999) *J Dent Res* 78, 673–80.
3. Ruch, J. V. (1998) *Biochem Cell Biol* 76, 923–38.
4. Couble, M. L., Farges, J. C., Bleicher, F., Perrat-Mabillon, B., Boudeulle, M. & Magloire, H. (2000) *Calcif Tissue Int* 66, 129–38.
5. Cheng, S. L., Yang, J. W., Rifas, L., Zhang, S. F. & Avioli, L. V. (1994) *Endocrinology* 134, 277–86.
6. Gronthos, S., Graves, S. E., Ohta, S. & Simmons, P. J. (1994) *Blood* 84, 4164–73.
7. Friedenstein, A. J., Ivanov-Smolenski, A. A., Chajlakjan, R. K., Gorskaya, U. F., Kuralesova, A. I., Latzinik, N. W. & Gerasimow, U. W. (1978) *Exp Hematol* 6, 440–4.
8. Bennett, J. H., Joyner, C. J., Triffitt, J. T. & Owen, M. E. (1991) *J Cell Sci* 99, 131–9.
9. Kuznetsov, S. A., Krebsbach, P. H., Satomura, K., Kerr, J., Riminucci, M., Benayahu, D. & Robey, P. G. (1997) *J Bone Miner Res* 12, 1335–47.
10. Ferrari, G., Cusella-De Angelis, G., Coletta, M., Paolucci, E., Stornaiuolo, A., Cossu, G. & Mavilio, F. (1998) *Science* 279, 1528–30.
11. Azizi, S. A. & et al. (1998) *Proc Natl Acad Sci USA.* 95, 3908–13.
12. Pittenger, M. F., Mackay, A. M., Beck, S. C., Jaiswal, R. K., Douglas, R., Mosca, J. D., Moorman, M. A., Simonetti, D. W., Craig, S. & Marshak, D. R. (1999) *Science* 284, 143–7.
13. Bianco, P. & Robey, P. G. (2000) *J. Clin. Invest.* 105.
14. Robey, P. G. (2000) *J Clin Invest* 105, 1489–91.
15. Nakashima, M., Nagasawa, H., Yamada, Y. & Reddi, A. H. (1994) *Dev Biol* 162, 18–28.
16. Shiba, H., Fujita, T., Doi, N., Nakamura, S., Nakanishi, K., Takemoto, T., Hino, T., Noshiro, M., Kawamoto, T., Kurihara, H. & Kato, Y. (1998) *J Cell Physiol* 174, 194–205.
17. Onishi, T., Kinoshita, S., Shintani, S., Sobue, S. & Ooshima, T. (1999) *Arch Oral Biol* 44, 361–71.
18. Kettunen, P., Karavanova, I. & Thesleff, I. (1998) *Dev Genet* 22, 374–85.
19. Kuo, M. Y., Lan, W. H., Lin, S. K., Tsai, K. S. & Hahn, L. J. (1992) *Arch Oral Biol* 37, 945–52.
20. Tsukamoto, Y., Fukutani, S., Shin-Ike, T., Kubota, T., Sato, S., Suzuki, Y. & Mori, M. (1992) *Arch Oral Biol* 37, 1045–55.
21. Buurma, B., Gu, K. & Rutherford, R. B. (1999) *Eur J Oral Sci* 107, 282–9.
22. Ritchie, H. H., Hou, H., Veis, A. & Butler, W. T. (1994) *J Biol Chem* 269, 3698–702.
23. Gorter de Vries, I., Quartier, E., Van Steirteghem, A., Boute, P., Coomans, D. & Wisse, E. (1986) *Arch Oral Biol* 31, 57–66.
24. MacDougall, M., Simmons, D., Luan, X., Nydegger, J., Feng, J. & Gu, T. T. (1997) *J Biol Chem* 272, 835–42.
25. Feng, J. Q., Luan, X., Wallace, J., Jing, D., Ohshima, T., Kulkarni, A. B., D'Souza, R. N., Kozak, C. A. & MacDougall, M. (1998) *J Biol Chem* 273, 9457–64.
26. Owen, M. E. (1998) (Combridge University Press, Cambridge), pp. 1–9.

27. Friedenstein, A. J. (1980) in *Immunology of Bone Marrow Transplantation* (Springer-Verlag, Berlin), pp. 19–29.
28. Bianco, P. & Cossu, G. (1999) *Exp Cell Res* 251, 257–63.
29. Bianco, P. & Riminucci, M. (1998) in *Marrow stromal cell culture*, eds. Owen, M. A. & Beresford, J. N. (Cambridge University Press, Cambridge UK), pp. 10–25.
30. Doherty, M. J., Ashton, B. A., Walsh, S., Beresford, J. N., Grant, M. E. & Canfield, A. E. (1998) *J Bone Miner Res* 13, 828–38.
31. Shiba, H., Nakamura, S., Shirakawa, M., Nakanishi, K., Okamoto, H., Satakeda, H., Noshiro, M., Kamihagi, K., Katayama, M. & Kato, Y. (1995) *Dev Biol* 170, 457–66.
32. Majors, A. K., Boehm, C. A., Nitto, H., Midura, R. J. & Muschler, G. F. (1997) *J Orthop Res.* 15, 546–57.
33. Ishizeki, K., Nawa, T. & Sugawara, M. (1990) *Anat Rec* 226, 279–87.
34. Holtgrave, E. A. & Donath, K. (1995) *Biomaterials* 16, 155–9.
35. Lyaruu, D. M., van Croonenburg, E. J., van Duin, M. A., Bervoets, T. J., Woltgens, J. H. & de Blieck-Hogervorst, J. M. (1999) *J Oral Pathol Med* 28, 293–6.
36. Prime, S. S., Sim, F. R. & Reade, P. C. (1982) *Transplantation* 33, 561–2.
37. Schultz, E. & McCormick, K. M. (1994) *Rev. Physiol. Biochem. Pharmacol.* 123, 213–257.
38. Johansson, C. B., Svensson, M., Wallstedt, L., Janson, A. M. & Frisen, J. (1999) *Exp Cell Res* 253, 733–6.
39. Doetsch, F., Caille, I., Lim, D. A., Garcia-Verdugo, J. M. & Alvarez-Buylla, A. (1999) *Cell* 97, 703–16.

TABLE 1

Immunohistochemical analysis of human DPSCs and BMSCs in vitro.

| Marker | DPSC-1 | DPSC-2 | BMSC |
|---|---|---|---|
| CD14 | − | − | − |
| CD34 | − | − | − |
| CD44 | ++ | ++ | ++ |
| CD45 | − | − | − |
| Integrin β1 | ++/+ | ++/+ | ++ |
| VCAM-1 | + | + | ++ |
| MyoD | − | − | − |
| α-SM actin | ++/− | ++/− | ++/+/− |
| Neurofilam. | − | − | − |
| MUC-18 | ++/− | ++/+/− | ++/+/− |
| Collagen-I | + | ++ | ++/+ |
| Collagen-II | − | − | − |
| Collagen-III | ++/+ | ++/+ | ++/+ |
| Osteocalcin | ++/+ | ++/+ | +/− |
| Osteonectin | ++/+ | ++ | ++/+ |
| BSP | − | − | +/− |
| Osteopontin | +/− | +/− | +/− |
| Alk Phos | ++/+/− | ++/+/− | ++/+/− |
| PPARγ | − | − | − |
| FGF-2 | ++/+ | ++ | ++/+ |

++ Strong staining,
+ Weak staining,
− Negative,
/ Subpopulation

What is claimed is:

1. A culture of isolated adult human dental pulp stem cells.

2. The culture of claim 1, wherein the stem cells can differentiate into odontoblasts.

3. The culture of claim 1, wherein the stem cells can regenerate a dentin/pulp structure in vivo.

4. The culture of claim 1, wherein the stem cells are not adipogenic.

5. The culture of claim 1, wherein the cells do not produce bone sialoprotein.

6. A method of regenerating human dentin/pulp tissue, comprising: a) contacting a cell from a culture of isolated adult human dental pulp stem cells with a mineral source; and b) transplanting the cell from step a) into a mammal.

7. The method of claim 6, wherein the mineral source is hydroxyapatite/tricalcium phosphate.

8. A method of producing human dentin/pulp tissue, comprising: a) contacting a cell from a culture of isolated adult human dental pulp stem cells with a mineral source; and b) transplanting the cell from step a) into a mammal.

9. The method of claim 8, wherein the mineral source is hydroxyapatite/tricalcium phosphate.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 1
ctatggagag gacgccacgc ctgg                                    24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 2
catagccatc gtagccttgt cct                                     23

<210> SEQ ID NO 3
<211> LENGTH: 16
<212> TYPE: DNA
<213> ORGANISM: Artificial Sequence -continued

```
<220> FEATURE:
<223> OTHER INFORMATION: Description of Artificial Sequence; Note =
      synthetic construct

<400> SEQUENCE: 3
catgagagcc ctcaca                                                    16

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 4
agagcgacac cctagac                                                   17

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 5
ggcagtgact caaaggagc                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 6
tgctgtcact gtcactgctg                                                20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 7
agccgcatct tcttttgcgt c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 8
tcatatttgg caggtttttc t                                              21
```